(12) United States Patent
Skog et al.

(10) Patent No.: US 10,421,977 B2
(45) Date of Patent: Sep. 24, 2019

(54) USE OF MICROVESICLES IN THE TREATMENT OF MEDICAL CONDITIONS

(71) Applicant: The General Hospital Corporation, Boston, MA (US)

(72) Inventors: Johan Karl Olov Skog, Lincoln, MA (US); Casey Maguire, Arlington, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 176 days.

(21) Appl. No.: 13/858,629

(22) Filed: Apr. 8, 2013

(65) Prior Publication Data
US 2013/0202559 A1 Aug. 8, 2013

Related U.S. Application Data

(63) Continuation of application No. 13/580,509, filed as application No. PCT/US2011/025861 on Feb. 23, 2011, now abandoned.

(60) Provisional application No. 61/307,213, filed on Feb. 23, 2010.

(51) Int. Cl.
| | |
|---|---|
| C12N 15/86 | (2006.01) |
| A61K 9/51 | (2006.01) |
| A61K 47/69 | (2017.01) |
| A61K 39/00 | (2006.01) |
| A61K 38/00 | (2006.01) |

(52) U.S. Cl.
CPC ............ *C12N 15/86* (2013.01); *A61K 9/5184* (2013.01); *A61K 47/6901* (2017.08); *A61K 38/00* (2013.01); *A61K 2039/5258* (2013.01); *C12N 2750/14143* (2013.01); *C12N 2750/14145* (2013.01); *C12N 2810/6081* (2013.01); *C12N 2810/855* (2013.01)

(58) Field of Classification Search
None
See application file for complete search history.

(56) References Cited

U.S. PATENT DOCUMENTS

| | | | |
|---|---|---|---|
| 4,196,191 A | 4/1980 | Almeida et al. | |
| 6,130,089 A | 10/2000 | Liszewicz | |
| 7,972,593 B2 * | 7/2011 | Tomatsu | C12N 9/96 424/93.2 |
| 2002/0168342 A1 | 11/2002 | Wang et al. | |
| 2008/0268429 A1 | 10/2008 | Pietrzkowski | |

FOREIGN PATENT DOCUMENTS

WO   WO 07/126386   * 11/2007 ............. C12N 15/87

OTHER PUBLICATIONS

Cocucci et al., Trends in Cell Biology, online Jan. 12, 2009, 19: 43-51.*
Sarukhan et al., J. Virol., 2001, 75: 269-277.*
Yu et al., Cancer Res., 2006, 66: 4795-4801.*
Pastorino et al., Cancer Res., 2006, 66: 10073-10082.*
Ma et al., Gene Therapy, 2002, 9: 2-11.*
Hill et al., J. Virol. Methods, 1999, 78: 177-189.*
Scherphof et al., Ann. N.Y. Acad. Sci., 1985, 368-384.*
Willekens et al., Blood, 2005, 105: 2141-2145.*
Wiley et al., Proc. Natl. Acad. Sci. U.S.A., 2006, 103: 738-743.*
Almqvist et al., Old Herbron University Seminar Monograph 22: Biological consequences of host-microbe interactions, 2009, p. 57-66.*
Mori et al., Traffic, 2008, 9: 1728-1742.*
Seow et al., Molecular Therapy, 2009, 17: 767-777.*
Yotnda et al., Mol. Ther. 2002, 5: 233-241.*
International Search Report for PCT/US2011/025861, dated Dec. 5, 2011.
Segura et al., "Purification and characterization of retrovirus vector particles by rate zonal ultracentrifugation." Journal of Virological Methods 133(1):82-91 (2006).

* cited by examiner

*Primary Examiner* — Ileana Popa
(74) *Attorney, Agent, or Firm* — Nixon Peabody LLP; David S. Resnick; Shayne Y. Huff

(57) ABSTRACT

This invention relates generally to populations of microvesicles containing or otherwise associated with viral particles, methods of producing these purified populations, and methods of using these purified populations in a variety of diagnostic, therapeutic and/or prophylactic indications.

24 Claims, 8 Drawing Sheets
Specification includes a Sequence Listing.

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Chemically synthesized probe

<400> SEQUENCE: 1
tgccagccat ctgttgtttg cc                                        22

<210> SEQ ID NO 2
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 2
cctcgactgt gccttctag                                            19

<210> SEQ ID NO 3
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 3
tgcgatgcaa tttcctcat                                            19

USE OF MICROVESICLES IN THE TREATMENT OF MEDICAL CONDITIONS

RELATED APPLICATIONS

This application is a continuation application of U.S. patent application Ser. No. 13/580,509, deposited on Aug. 22, 2012 as a national stage application, filed under 35 U.S.C. § 371, of International Application No. PCT/US2011/025861, filed Feb. 23, 2011, which claims the benefit of U.S. Provisional Application No. 61/307,213, filed Feb. 23, 2010, the contents of each of which are hereby incorporated by reference in their entirety.

FIELD OF THE INVENTION

The invention provides purified populations of microvesicles containing or otherwise associated with viral particles, methods of producing these purified populations, and methods of using these purified populations in a variety of diagnostic, therapeutic and/or prophylactic indications.

INCORPORATION OF SEQUENCE LISTING

The contents of the text file named "41432-205N01US_ST25", which was created on Apr. 8, 2013 and is 1008 bytes in size, are hereby incorporated by reference in their entirety.

BACKGROUND OF THE INVENTION

Microvesicles are shed by eukaryotic cells, or budded off of the plasma membrane, to the exterior of the cell. These membrane vesicles are heterogeneous in size with diameters ranging from about 10 nm to about 5000 nm. The small microvesicles (approximately 10 to 1000 nm, and more often 30 to 200 nm in diameter) that are released by exocytosis of intracellular multivesicular bodies are sometimes referred to in the art as "microvesicles." Microvesicles contain nucleic acids that have been used as biomarkers for medical diagnosis, prognosis and therapy evaluation.

There exists a need to further investigate the characteristics of microvesicles and to exploit the capabilities of these microvesicles in a variety of therapeutic and prophylactic indications.

SUMMARY OF THE INVENTION

The purified populations, compositions and methods of the invention use naturally secreted microvesicles to encapsulate, coat or otherwise associate with a viral vector particle to produce a microvesicle-associated vector, referred to herein as "MAV". For example, the viral particle can be encapsulated within a microvesicle, the viral particle can be associated with the microvesicle lipid membrane, the viral vector can be associated with one or more types of membrane-bound proteins or receptors on the microvesicle surface and/or interior, or any combination of these associations can be used to produce a MAV. The association between the microvesicle and the viral particle can be a covalent interaction or a non-covalent interaction.

The association between the microvesicle and the viral particle protects or otherwise shields the viral particle. For example, the microvesicle shields the viral particle from an anti-virus immune response in vivo. The association between the microvesicle and the viral particle prevents or otherwise impedes the ability of neutralizing antibodies and/or complement components in a subject to bind or otherwise interact with the viral particle. Depending on the microvesicle type, the microvesicle components, including, for example, cytokines, cell surface receptors, may abrogate cytotoxic immunity against vector transduced cells types.

The purified populations of microvesicles associated with a viral particle are useful to deliver a nucleic acid to a cell. In some embodiments, the cell is within the body of an individual. The cell to which the nucleic acid gets delivered is referred to as the target cell. The viral particle can be engineered to contain a nucleic acid that it would not naturally contain (i.e. which is exogenous to the normal content of the viral particle). In some embodiments, the cell which produces the microvesicle for administration is of the same or similar origin or location in the body as the target cell. For example, for delivery of a microvesicle to a brain cell, the cell which produces the microvesicle would be a brain cell (e.g. a primary cell grown in culture). In other embodiments, the cell which produces the microvesicle is of a different cell type than the target cell. In one embodiment, the cell which produces the microvesicle is a type that is located proximally in the body to the target cell.

The nucleic acid sequence which can be delivered to a cell via a microvesicle and associated viral vector can be RNA or DNA, and can be single or double stranded, and can be selected from a group comprising: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequences encoding proteins, for example that act as transcriptional repressors, antisense molecules, ribozymes, small inhibitory nucleic acid sequences, for example but are not limited to RNAi, shRNA, siRNA, miRNA, antisense oligonucleotides, and combinations thereof. The nucleic acid sequence can include or be accompanied by accessory nucleic acid sequences, i.e., sequences needed for the expression of the nucleic acid sequence. These accessory nucleic acid sequences include, for example, promoters, positive regulatory elements and negative regulatory elements.

The microvesicles are shed from cells referred to herein as "producer cells." The producer cells can naturally shed one or more types of microvesicles. Alternatively or in addition, the producer cells can be modified, e.g., genetically engineered or otherwise modified using compounds that can affect microvesicle secretion and/or production, to shed one or more desired types of microvesicles.

Suitable producer cells for use in the purified microvesicle populations, compositions and methods of the invention include, by way of non-limiting example, cells such as 293T (ATCC, see also Biotechniques. 2003 January; 34(1):184-9); Per.C6 (Crucell), AGE1.CR (ProBioGen AG); AGE1.HN® cell line (ProBioGen AG); and KG-1 cells (ATCC, see also Biochem Biophys Res Commun. 2005 Aug. 5; 333(3):896-907), which can be differentiated into human dendritic cells. Suitable producer cells also include tumor cells such as cells from ovarian cancer, glioma, hepatocarcinoma (see e.g., PLoS One. 2010 Jul. 22; 5(7):e11469), as tumor-derived microvesicles have been shown to have immunosuppressive properties and can be useful for long-term expression of a transgene. Suitable producer cells also include regulatory T cell lines such as CD4+ CD25+ T cells (see e.g., Blood. 2005 Nov. 1; 106(9):3068-73. Epub 2005 Jul. 14), which can be useful for long-term expression of a transgene.

In some embodiments, the lipid membrane of the microvesicle is modified to enhance or otherwise alter a property of the microvesicle, such as, for example, target cell type, cell activation, or a transduction property. For example, the expression or presence of a cell surface protein found on the microvesicle can be altered to induce a change in the microvesicle. In some embodiments, the surface of the microvesicle can be modified to include a receptor ligand that targets a desired cell type or a bridging molecule linked to a receptor ligand that targets a desired cell type.

In some embodiments, the lipid membrane of the microvesicle can be modified to express or include Biotin acceptor peptide-transmembrane (BAP-TM) on its lipid membrane (see e.g., Tannous et al. Nat Methods. 2006 May; 3(5):391-6). The use of BAP-TM allows for display of any biotinylated ligand or other protein on the membrane surface via a streptavidin bridge, as BAP is genetically fused with PDGR transmembrane domain and gets biotinylated using BirA expression.

In some embodiments, the lipid membrane of the microvesicle can be modified to express or include streptavidin-conjugated magnetic nanoparticles (see e.g., J Neurosci Methods. 2011 Jan. 15; vol. 194(2):316-20). The use of streptavidin-conjugated magnetic nanoparticles links magnetic particles to BAP-TM and then directs the microvesicle to wherever a strong magnet is placed.

In some embodiments, the lipid membrane of the microvesicle can be modified to express or include the membrane proteins from enveloped viruses. For example, vesicular stomatitis virus glycoprotein G (VSV-G) (see e.g., Proc. Natl. Acad. Sci. USA Vol. 93, pp. 15266-15271, December 1996) can be used to pseudotype lentivirus and retrovirus vectors, and VSV-G gives broad cell tropism. The use of VSV-G allows for robust transgene expression in a variety of cultured cells as well as gene expression in vivo.

In some embodiments, the lipid membrane of the microvesicle can be modified to express or include transferrin mimic peptide (CRTIGPSVC) (see e.g., J Clin Invest. 2011 Jan. 4; 121(1):161-73). CRTIGPSVC is useful in treating disorders of the brain, such as, for example, brain tumors, because CRTIGPSVC is able to cross the blood-brain barrier. CRTIGPSVC binds to transferrin receptor expressed on brain and brain tumor vasculature. Biotinylated CRTIGPSVC can be linked to BAP-TM via a streptavidin bridge.

In some embodiments, the lipid membrane of the microvesicle can be modified to express or include a transmembrane bound single chain antibody against EGFRvIII, which is overexpressed on many human glioma tumors. EGFRvIII can be used as a target for gene therapy-mediated killing of glioma cells.

In some embodiments, the lipid membrane of the microvesicle can be modified to express or include CD40 ligand (CD40L), which is specific for CD40 expressed on the surface of dendritic cells and B cells. The use of the CD40/CD40L interaction may enhance antigen presentation of vectored antigens.

In some embodiments, the lipid membrane of the microvesicle can be modified to express or include Rabies derived peptide (see e.g., Nature. 2007 Jul. 5; 448(7149): 39-43. Epub 2007 Jun. 17). Rabies derived peptide binds to acetylcholine receptor on neurons and can be useful for targeting therapeutic molecules to the CNS.

The microvesicles in the purified populations provided herein contain or are otherwise associated with the viral particles to produce a MAV. The characteristic of a MAV according to the invention is a viral particle, e.g., viral capsid, that contains a nucleic acid encoding a gene of interest, where the MAV is further surrounded by or otherwise associated with a membrane derived from a virus-producing cell. For example, the MAV is or is derived from adenovirus, including replication defective and competent vectors; lentivirus; retrovirus; herpes virus, including replication defective and competent vectors; adeno-associated virus (AAV); alphavirus, including, for example, sindbis virus, semliki forest virus, Venezuelan equine encephalitis virus, Ross River virus; flavivirus vectors; baculovirus; bacteriophage; orthomyxovirus (influenza); vaccinia; human papilloma virus, including, for example, virus like particles; and paramyxovirus, including, for example, Newcastle disease virus vectors.

These viral particles are useful in a variety of applications such as, for example, gene transfer applications, including gene replacement, gene repair, and/or mRNA knockdown therapeutic applications, and vaccine applications. These MAV are useful in gene transfer applications where conventional viral vectors including, for example, conventional AAV vectors, are inefficient or incapable of infection of a target cell or tissue type.

In some embodiments, the vector in the MAV is an adeno-associated viral (AAV) vector. The AAV capsids are incorporated into microvesicles that can be purified from the supernatant of the producer cell line. These microvesicles are fully competent for transduction of cells in culture as well as in vivo. In vivo delivery of the vector is markedly enhanced with the associated microvesicles and extended to multiple tissues compared to AAV capsids of those same serotypes as assessed by in vivo bioluminescence imaging.

The purified populations of microvesicles and compositions containing these purified populations are useful in a variety of therapeutic indications. The ability of vector producer cells to insert viral particles inside microvesicles or the vector's association with microvesicles components (on the surface and/or interior) offer many opportunities for gene therapy applications. First, the viral vector may be co-delivered with therapeutic proteins, mRNA or microRNA inside the microvesicle. The microvesicles are useful for enhancing the potency and bioavailability of a poorly soluble anti-inflammatory drug (see e.g., Mol Ther. 2010 September; 18(9):1606-14. Epub 2010 Jun. 22). Second, as other viral particles, e.g. HIV, can be packaged in or otherwise associated with microvesicles (see e.g., PNAS, Jan. 17, 2006, vol. 103, no. 3: 738-743), the purified populations, compositions and methods of the invention use other gene therapy vectors, e.g. adenovirus, lentivirus, to obtain novel microvesicle gene delivery vehicles. Packaging within or other association with microvesicle membranes has several advantages, as it allows targeting molecules incorporated into the plasma membrane to be used for targeting of the microvesicles, and furthermore, the microvesicles may shield the particle from pre-existing neutralizing antibodies or T cells in vivo. Microvesicles have been observed to have both immunogenic and immunosuppressive activities depending on the donor cell type, they can be used to obtain higher immune responses in vaccination strategies, or in cases where immune responses to the virus proteins may be problematic, microvesicles with immunosuppressive properties can be used.

In some embodiments, the purified populations and compositions provided herein are useful in the treatment of a cancer or other neoplastic condition, such as, for example, gliomas and other cancers of the central nervous system.

In some embodiments, the purified populations of microvesicles associated with a packaged or otherwise associated viral vector is an ingredient (e.g., population of MAV as the active ingredient) in a pharmaceutically acceptable composition and/or formulation suitable for administration to the subject. Generally these compositions and formulations comprise a pharmaceutically acceptable carrier for the active ingredient. The specific carrier will depend upon a number of factors, including for example, the route of administration.

In some embodiments, the invention includes a purified population of microvesicles that contain or are otherwise associated with one or more viral particles, wherein the microvesicle is shed or otherwise produced by a producing cell. In some embodiments, the microvesicles are associated with the viral particles through a covalent interaction. In some embodiments, the microvesicles are associated with the viral particles through a non-covalent interaction. In some embodiments, the producer cell naturally sheds the microvesicles. In some embodiments, the producer cell has been modified to shed the microvesicles. In some embodiments, the viral particle is or is derived from adenovirus, lentivirus, herpes virus, and adeno-associated virus (AAV). In some embodiments, the microvesicle comprises a lipid membrane having an outer surface that has been modified to include or express a receptor ligand or bridging molecule linked to a receptor ligand that targets a desired cell type. In some embodiments, the desired target cell type is different that the cell type that is target by a microvesicle having an unmodified lipid membrane. In some embodiments, the population of microvesicles comprises about $10^9$ to $10^{13}$ genome copies. In some embodiments, the viral particle comprises a nucleic acid encoding a peptide, polypeptide or protein. In some embodiments, the viral particle comprises a non-native nucleic acid.

In some embodiments, the invention provides methods of producing a purified population of microvesicles that contain viral particles by engineering a cell that sheds microvesicles, wherein the cell is engineered to comprise a viral vector and a nucleic acid encoding a desired polypeptide under the control of the viral nucleic acids necessary for expression of the desired polypeptide. The nucleic acid sequence can include or be accompanied by accessory nucleic acid sequences, i.e., sequences needed for the expression of the nucleic acid sequence. These accessory nucleic acid sequences include, for example, promoters, positive regulatory elements and negative regulatory elements. In some embodiments, the method also includes the step of increasing production of microvesicles by exposing the engineered cell to a stimulus or by genetically engineering the engineered cell to increase production of the microvesicles. In some embodiments, the stimulus is a chemical stressor or an environmental stressor. In some embodiments, the method also includes the step of increasing transfection efficiency of the viral particles. In some embodiments, the engineered cell is further modified to express a targeting protein on an outer surface of the microvesicle.

In some embodiments, the invention provides uses of the purified populations of microvesicles that are associated with viral particles in the treatment of a disorder in a subject. In some embodiments, the subject is human. In some embodiments, the disorder is a cancer. In some embodiments, the cancer is a cancer of the central nervous system (CNS).

BRIEF DESCRIPTION OF THE DRAWINGS

FIGS. 4A and 4B depict the isolation and identification of AAV1 MAV, while FIGS. 4C-4E depict the isolation and identification of AAV2 MAV.

DETAILED DESCRIPTION

Figure 1:
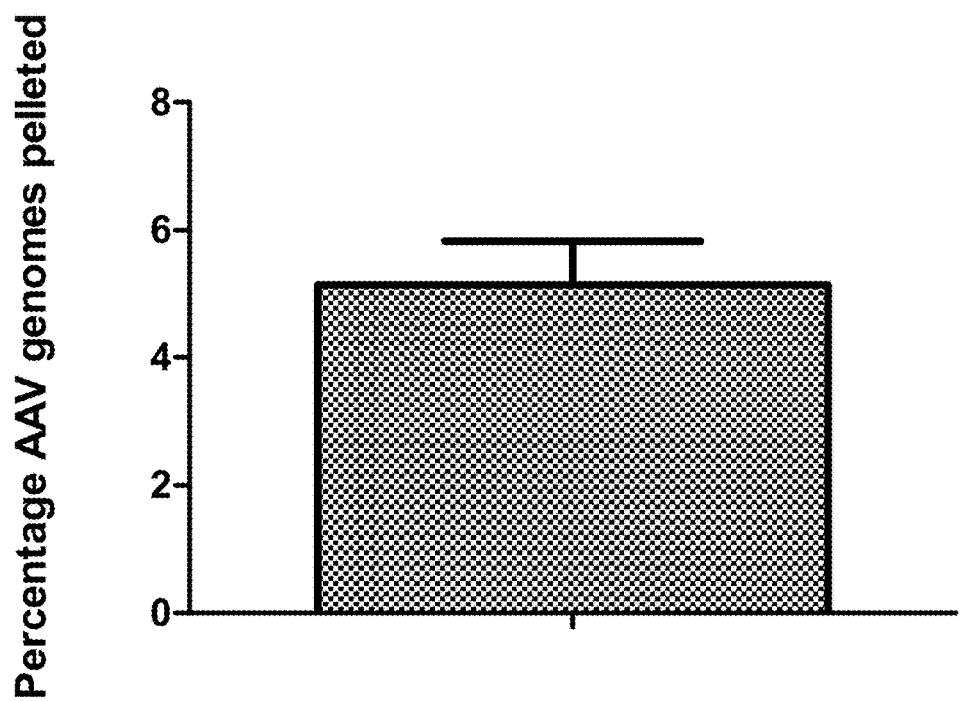
FIG. 1 is a graph depicting how AAV purified by standard techniques does not pellet efficiently using the centrifugation speed used for microvesicle pelleting.

The purified populations, compositions and methods described herein provide efficient and effective gene delivery systems based on viral vectors and microvesicles.

Microvesicles are shed by eukaryotic cells, or budded off of the plasma membrane, to the exterior of the cell. These membrane vesicles are heterogeneous in size with diameters ranging from about 10 nm to about 5000 nm. The small microvesicles (approximately 10 to 1000 nm, and more often 30 to 200 nm in diameter) that are released by exocytosis of intracellular multivesicular bodies are sometimes referred to in the art as "microvesicles." The methods and compositions described herein are equally applicable to microvesicles of all sizes; preferably 30 to 800 nm; and more preferably 30 to 200 nm. In some of the literature, the term "microvesicle" also refers to protein complexes containing exoribonucleases which are involved in mRNA degradation and the processing of small nucleolar RNAs (snoRNAs), small nuclear RNAs (snRNAs) and ribosomal RNAs (rRNA) (see e.g., Liu et al., "Reconstitution, activities, and structure of the eukaryotic RNA microvesicle," Cell, vol. 127:1223-37 (2006); van Dijk et al., "Human cell growth requires a functional cytoplasmic microvesicle, which is involved in various mRNA decay pathways," RNA, vol. 13:1027-35 (2007)). Such protein complexes do not have membranes and are not "microvesicles" or "microvesicles" as those terms are used herein.

Microvesicles are shed from both normal and malignant cells. Microvesicles have been found in bodily fluids such as blood, milk, ascites, urine and saliva among other fluids. The interior content of the microvesicles vary between cell types. The membrane surrounding the microvesicles, also referred to herein as the exterior content of the microvesicles, varies between cell types. The exterior content of the microvesicle can be modulated or otherwise manipulated to achieve a desired biological activity, such as, for example, targeting the microvesicle to a specific cell type.

Small microvesicles shed by cells are known as "microvesicles" (Thery et al., 2002). Microvesicles are reported as having a diameter of approximately 30-100 nm and are shed from many different cell types under both normal and pathological conditions (Thery et al., "Microvesicles: composition, biogenesis and function," Nat Rev Immunol., vol. 2:569-79 (2002)). Microvesicles are classically formed from the inward invagination and pinching off of the late endosomal membrane. This results in the formation of a multivesicular body (MVB) laden with small lipid bilayer vesicles (~40-100 nm in diameter), each of which contains a sample of the parent cell's cytoplasm (Stoorvogel et al., "The biogenesis and functions of microvesicles," Traffic, vol. 3:321-30 (2002)). Fusion of the MVB with the cell membrane results in the release of these microvesicles from the cell, and their delivery into the blood, urine or other bodily fluids.

Another category of cell-derived vesicles are known as "shedding microvesicles" (Cocucci et al., "Shedding microvesicles: artefacts no more," Trends Cell Biol., vol. 19:43-51 (2009)). These shedding microvesicles, formed by directly budding off of the cell's plasma membrane, are often heterogeneous in size, and like microvesicles, also contain a sample of the parent cell's cytoplasm. Microvesicles and shedding microvesicles co-isolate using ultracentrifugation and ultrafiltration isolation techniques and will, therefore, be collectively referred to here as microvesicles.

Vectors based on viruses have shown to be efficient means for gene delivery both to cultured cells and in animal models of human disease. However, limitations to viral vector-mediated gene transfer still exist, including off-target gene delivery/toxicity, inefficient gene delivery to some cell types, excessive vector uptake by non-target organs, and pre-existing humoral and cell-mediated immunity to the virion capsid. For example, several barriers to efficient gene delivery to the central nervous system (CNS) exist, including, for example, pre-existing immunity to the virus and/or transgene products, the lack of specific receptors on target cell; inefficient or impeded cellular entry/intracellular trafficking to the nucleus; and the tight junctions of the blood-brain barrier.

The composition and methods provided herein are designed to overcome these limitations. The compositions and methods include a viral vector, such as an adenovirus-based vector (replication defective and competent vectors), a lentivirus-based vector, a herpes virus based vector (replication defective and competent vectors), and adeno-associated virus based vectors.

The studies provided herein demonstrate that microvesicles isolated from cell culture media, e.g., cell culture media of adeno-associated virus (AAV) producer cells contain AAV virions. These results were confirmed by electron microscopy. These studies have also demonstrated that these microvesicle fractions containing AAV virons are capable of gene transfer to mammalian cells.

The characteristics of the adeno-associated virus (AAV) allow for its use in the methods and compositions provided herein. AAV is a tiny non-enveloped virus having a 25 nm capsid. No disease is known or has been shown to be associated with the wild type virus. AAV has a single-stranded DNA (ssDNA) genome. The insert capacity of the AAV virus is approximately 4.6 kb. AAV has been shown to exhibit long-term episomal transgene expression, and AAV has demonstrated excellent transgene expression in the brain, particularly in neurons. In addition, AAV can exhibit retrograde transport, i.e., from axons to cell body. There are numerous alternative AAV variants (over 100 have been cloned), and AAV variants have been identified based on desirable characteristics. For example, AAV9 has been shown to efficiently cross the blood-brain barrier. Moreover, the AAV capsid can be genetically engineered to increase transduction efficient and selectivity, e.g., biotinylated AAV vectors, directed molecular evolution, self-complementary AAV genomes and so on.

AAV gene therapy is currently being used in treatment of several central nervous system disorders (e.g., Parkinson's disease, Alzheimer's disease and glioma). For example, in one study, six Parkinson's patients received injection of AAV vector containing aromatic L-amino acid decarboxylase (AADC) gene, and transfer of AADC into the putamen. 96 weeks of AADC expression was observed (increased 56%), and motor function improved 46%. In another study of children with Leber's congenital amaurosis (leads to blindness), all children gained ambulatory vision, and one child gained light sensitivity equal to that of normal individuals.

Vectors based on adeno-associated virus (AAV) have shown remarkable efficiency for gene delivery both to cultured cells and in animal models of human disease. However, limitations to AAV vector-mediated gene transfer still exist, including off-target gene delivery/toxicity, inefficient gene delivery to some cell types, excessive vector uptake by non-target organs, such as liver uptake of AAV after intravenous injection, and pre-existing humoral and cell-mediated immunity to the virion capsid, which can abrogate gene delivery and expression in target tissues.

The methods provided herein address the limitations of using AAV vectors for gene transfer through the use of microvesicles. The characteristics of microvesicles are well suited for the compositions and methods provided herein. A microvesicle is small, nanometers in size, and can contain DNA, mRNA and microRNA (miRNA). Microvesicles contain a lipid membrane and host proteins that are recognized as self by the immune system. Microvesicles can encapsulate or otherwise package a wide variety of molecules, including nucleic acids and proteins. The microvesicles used in the compositions and methods provided herein are useful for shielding the viral capsid from pre-existing neutralizing antibodies.

The microvesicles and associated viral vector are produced and purified using methods that differ from the standard procedure for the production of viral vectors such as AAV. In the standard procedure for AAV production, the AAV vectors are produced by triple transfection of 293T cells with plasmids encoding for structural, nonstructural, and helper virus genes required for replication and virus production, and then, the virus is harvested and purified from cell lysates and the media is discarded. In the methods and studies described herein, the media from producer cells (i.e., cells that produce and shed microvesicles) is harvested, rather than the cells. The microvesicles in the media are pelleted, the pellet is resuspended and then loaded onto a density gradient. The fractions are collected and analyzed.

In the studies provided herein, the natural ability of cells to secrete microvesicles was exploited. Following transfection of 293T cells with an AAV2 vector construct and capsid expression cassettes in a standard vector production paradigm, it was discovered that a substantial fraction of AAV virons released from the cells were within microvesicles, e.g., AAV-microvesicles. Intact AAV capsids within individual microvesicles were observed by transmission electron microscopy.

The studies presented herein also demonstrate that viral vectors such as AAV vectors can be packaged inside or otherwise associated microvesicles (see e.g., FIGS. 4A-4E). In mice, intravenous injection of microvesicles associated with AAV2 encoding a luminescent reporter (firefly luciferase) gave higher whole-body luminescence, as well as unique tissue selectivity compared to the standard-purified AAV2 vector (see e.g., FIGS. 3A, 3B). Microvesicles represent a unique gene delivery entity that improves virus vector-based gene therapy.

The studies described herein demonstrate that under normal AAV production conditions a detectable amount of AAV virions are associated with microvesicles which bud off the surface of the cells into the medium. These microvesicle-associated AAV vectors, termed AAV MAVs, were capable of gene transfer in cultured cells and vastly surpassed standard AAV vectors of the same serotype both in level and distribution of gene expression in mice in vivo as assessed by bioluminescence imaging following i.v. injection. The global gene expression observed for AAV2-Fluc microvesicles (FIGS. 3A, 3B) was striking as AAV2 has been shown to mediate relatively low expression levels restricted mainly to the liver even at high doses. In contrast, for AAV2-Fluc microvesicles, strong expression was seen in the liver with signal over the entire animal as early as two weeks and at a low dose ($4.4 \times 10^9$ gc/animal).

The purified populations, compositions and methods provided herein utilize a novel pathway by which viral vectors, including, for example, AAV vectors, are exported from producer cells via an association with microvesicles. Isolation and characterization of these packaged or otherwise associated viral vectors (MAV) showed that they displayed in vivo gene delivery properties superior to standard viral vectors purified by standard techniques. The use of packaged or otherwise associated viral vectors (MAV) improves the use of this vector platform both as a tool of molecular biology as well as a gene therapy vector.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the human heavy chain immunoglobulin molecules and the human light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the nucleic acid sequences are contemplated as being encompassed by the present invention, providing that the variations in the nucleic acid sequence maintain at least 75%, more preferably at least 80%, 90%, 95%, and most preferably 99%.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

The term "promoter sequence" as used herein shall mean a polynucleotide sequence comprising a region of a gene at which initiation and rate of transcription are controlled. A promoter sequence comprises an RNA polymerase binding site as well as binding sites for other positive and negative regulatory elements. Positive regulatory elements promote the expression of the gene under control of the promoter sequence. Negative regulatory elements repress the express of the gene under control of the promoter sequence. Promoter sequences used herein are found either upstream or internal to the gene being regulated. Specifically, the term "first promoter sequence" versus "second promoter sequence" refers to the relative position of the promoter sequence within the expression vector. The first promoter sequence is upstream of the second promoter sequence.

The term "endogenous gene" as used herein shall mean a gene encompassed within the genomic sequence of a cell. The term "exogenous gene" as used herein shall mean a gene not encompassed within the genomic sequence of a cell. Exogenous genes are introduced into cells by the instant methods. The term "transgene" as used herein shall mean a gene that has been transferred from one organism to another.

The term "transfection" as used herein shall mean the transportation across the cell membrane or insertion of one or more DNA compositions into a cell. "Stable transfection" as used herein shall mean the generation, under selective pressure, of isolated protein-expressing cell lines. "Semi-stable transfection" as used herein shall mean the generation, under selective pressure, of a mixture of protein-expressing cell lines. "Transient transfection" as used herein shall mean the generation, without selective pressure, of protein-expressing cell lines. Stable and semi-stable transfections may lead to incorporation of transfected sequences into the genome due to selective pressure. Transient transfections do not lead to genomic incorporation of transfected sequences and typically retain these sequences for a shorter period of time. The term "transfection-resistant" as used herein shall mean transfected with low efficiency or success using known methods.

The term "reporter gene" as used herein shall mean a polynucleotide sequence encoding for a polypeptide that creates a physical change in those cells which incorporate the expression vector, and, thus, the gene of interest. Physical changes are often color changes or fluorescence.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As used herein, a "bodily fluid" refers to a sample of fluid isolated from anywhere in the body of the subject, preferably a peripheral location, including but not limited to, for example, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof.

The term "subject" is intended to include all animals shown to or expected to have microvesicles. In particular embodiments, the subject is a mammal, a human or nonhuman primate, a dog, a cat, a horse, a cow, other farm animals, or a rodent (e.g. mice, rats, guinea pig. etc.). The term "subject" and "individual" are used interchangeably herein.

Methods of isolating microvesicles from a biological sample are known in the art. For example, a method of differential centrifugation is described in a paper by Raposo et al. (Raposo et al., 1996), and similar methods are detailed in the Examples section herein. Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in (Taylor and Gercel-Taylor, 2008). A method of nanomembrane ultrafiltration concentrator is described in (Cheruvanky et al., 2007).

Preferably, microvesicles can be identified and isolated from bodily fluid of a subject by a newly developed microchip technology that uses a unique microfluidic platform to efficiently and selectively separate tumor derived microvesicles. This technology, as described in a paper by Nagrath et al. (Nagrath et al., 2007), can be adapted to identify and separate microvesicles using similar principles of capture and separation as taught in the paper. Each of the foregoing references is incorporated by reference herein for its teaching of these methods.

In one embodiment, the microvesicles isolated from a bodily fluid are enriched for those originating from a specific cell type, for example, lung, pancreas, stomach, intestine, bladder, kidney, ovary, testis, skin, colorectal, breast, prostate, brain, esophagus, liver, placenta, fetus cells. Because the microvesicles often carry surface molecules such as antigens from their donor cells, surface molecules may be used to identify, isolate and/or enrich for microvesicles from a specific donor cell type (Al-Nedawi et al., 2008; Taylor and Gercel-Taylor, 2008). In this way, microvesicles originating from distinct cell populations can be analyzed for their nucleic acid content. For example, tumor (malignant and non-malignant) microvesicles carry tumor-associated surface antigens and may be detected, isolated and/or enriched via these specific tumor-associated surface antigens. In one example, the surface antigen is epithelial-cell-adhesion-molecule (EpCAM), which is specific to microvesicles from carcinomas of lung, colorectal, breast, prostate, head and neck, and hepatic origin, but not of hematological cell origin (Balzar et al., 1999; Went et al., 2004). In another example, the surface antigen is CD24, which is a glycoprotein specific to urine microvesicles (Keller et al., 2007). In yet another example, the surface antigen is selected from a group of molecules CD70, carcinoembryonic antigen (CEA), EGFR, EGFRvIII and other variants, Fas ligand, TRAIL, transferrin receptor, p38.5, p97 and HSP72. Additionally, tumor specific microvesicles may be characterized by the lack of surface markers, such as CD80 and CD86.

The isolation of microvesicles from specific cell types can be accomplished, for example, by using antibodies, aptamers, aptamer analogs or molecularly imprinted polymers specific for a desired surface antigen. In one embodiment, the surface antigen is specific for a cancer type. In another embodiment, the surface antigen is specific for a cell type which is not necessarily cancerous. One example of a method of micro vesicle separation based on cell surface antigen is provided in U.S. Pat. No. 7,198,923. As described in, e.g., U.S. Pat. Nos. 5,840,867 and 5,582,981, WO/2003/050290 and a publication by Johnson et al. (Johnson et al., 2008), aptamers and their analogs specifically bind surface molecules and can be used as a separation tool for retrieving cell type-specific microvesicles. Molecularly imprinted polymers also specifically recognize surface molecules as described in, e.g., U.S. Pat. Nos. 6,525,154, 7,332,553 and 7,384,589 and a publication by Bossi et al. (Bossi et al., 2007) and are a tool for retrieving and isolating cell type-specific microvesicles. Each of the foregoing reference is incorporated herein for its teaching of these methods.

It may be beneficial or otherwise desirable to extract the nucleic acid from the microvesicles for analysis. Nucleic acid molecules can be isolated from a microvesicle using any number of procedures, which are well-known in the art, the particular isolation procedure chosen being appropriate for the particular biological sample. In some instances, with some techniques, it may also be possible to analyze the nucleic acid without extraction from the microvesicle.

In one embodiment, the extracted nucleic acids, including DNA and/or RNA, are analyzed directly without an amplification step. Direct analysis may be performed with different methods including, but not limited to, the nanostring technology. NanoString technology enables identification and quantification of individual target molecules in a biological sample by attaching a color coded fluorescent reporter to each target molecule. This approach is similar to the concept of measuring inventory by scanning barcodes.

Reporters can be made with hundreds or even thousands of different codes allowing for highly multiplexed analysis. The technology is described in a publication by Geiss et al. (Geiss et al., 2008) and is incorporated herein by reference for this teaching.

In another embodiment, it may be beneficial or otherwise desirable to amplify the nucleic acid of the microvesicle prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a profile as described below.

In one embodiment, the extracted nucleic acid is RNA. RNAs are then preferably reverse-transcribed into complementary DNAs before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self sustained sequence replication and its variants (Guatelli et al., 1990), transcriptional amplification system and its variants (Kwoh et al., 1989), Qb Replicase and its variants (Miele et al., 1983), cold-PCR (Li et al., 2008) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods.

Diseases or other medical conditions for which the inventions described herein are applicable include, but are not limited to, nephropathy, diabetes insipidus, diabetes type I, diabetes II, renal disease glomerulonephritis, bacterial or viral glomerulonephritides, IgA nephropathy, Henoch-Schonlein Purpura, membranoproliferative glomerulonephritis, membranous nephropathy, Sjogren's syndrome, nephrotic syndrome minimal change disease, focal glomerulosclerosis and related disorders, acute renal failure, acute tubulointerstitial nephritis, pyelonephritis, GU tract inflammatory disease, Pre-clampsia, renal graft rejection, leprosy, reflux nephropathy, nephrolithiasis, genetic renal disease, medullary cystic, medullar sponge, polycystic kidney disease, autosomal dominant polycystic kidney disease, autosomal recessive polycystic kidney disease, tuberous sclerosis, von Hippel-Lindau disease, familial thin-glomerular basement membrane disease, collagen III glomerulopathy, fibronectin glomerulopathy, Alport's syndrome, Fabry's disease, Nail-Patella Syndrome, congenital urologic anomalies, monoclonal gammopathies, multiple myeloma, amyloidosis and related disorders, febrile illness, familial Mediterranean fever, HIV infection-AIDS, inflammatory disease, systemic vasculitides, polyarteritis nodosa, Wegener's granulomatosis, polyarteritis, necrotizing and crecentic glomerulonephritis, polymyositis-dermatomyositis, pancreatitis, rheumatoid arthritis, systemic lupus erythematosus, gout, blood disorders, sickle cell disease, thrombotic thrombocytopenia purpura, Fanconi's syndrome, transplantation, acute kidney injury, irritable bowel syndrome, hemolytic-uremic syndrome, acute corticol necrosis, renal thromboembolism, trauma and surgery, extensive injury, burns, abdominal and vascular surgery, induction of anesthesia, side effect of use of drugs or drug abuse, circulatory disease myocardial infarction, cardiac failure, peripheral vascular disease, hypertension, coronary heart disease, non-atherosclerotic cardiovascular disease, atherosclerotic cardiovascular disease, skin disease, psoriasis, systemic sclerosis, respiratory disease, COPD, obstructive sleep apnoea, hypoia at high altitude or erdocrine disease, acromegaly, diabetes mellitus, or diabetes insipidus.

The cancer diagnosed, monitored or otherwise profiled, can be any kind of cancer. This includes, without limitation, epithelial cell cancers such as lung, ovarian, cervical, endometrial, breast, brain, colon and prostate cancers. Also included are gastrointestinal cancer, head and neck cancer, non-small cell lung cancer, cancer of the nervous system, kidney cancer, retina cancer, skin cancer, liver cancer, pancreatic cancer, genital-urinary cancer and bladder cancer, melanoma, and leukemia. In addition, the methods and compositions of the present invention are equally applicable to detection, diagnosis and prognosis of non-malignant tumors in an individual (e.g. neurofibromas, meningiomas and schwannomas).

In some embodiments, the cancer is brain cancer. Types of brain tumors and cancer are well known in the art. Glioma is a general name for tumors that arise from the glial (supportive) tissue of the brain. Gliomas are the most common primary brain tumors. Astrocytomas, ependymomas, oligodendrogliomas, and tumors with mixtures of two or more cell types, called mixed gliomas, are the most common gliomas. The following are other common types of brain tumors: Acoustic Neuroma (Neurilemmoma, Schwannoma. Neurinoma), Adenoma, Astracytoma, Low-Grade Astrocytoma, giant cell astrocytomas, Mid- and High-Grade Astrocytoma, Recurrent tumors, Brain Stem Glioma, Chordoma, Choroid Plexus Papilloma, CNS Lymphoma (Primary Malignant Lymphoma), Cysts, Dermoid cysts, Epidermoid cysts, Craniopharyngioma, Ependymoma Anaplastic ependymoma, Gangliocytoma (Ganglioneuroma), Ganglioglioma, Glioblastoma Multiforme (GBM), Malignant Astracytoma, Glioma, Hemangioblastoma, Inoperable Brain Tumors, Lymphoma, Medulloblastoma (MDL), Meningioma, Metastatic Brain Tumors, Mixed Glioma, Neurofibromatosis, Oligodendroglioma. Optic Nerve Glioma, Pineal Region Tumors, Pituitary Adenoma, PNET (Primitive Neuroectodermal Tumor), Spinal Tumors, Subependymoma, and Tuberous Sclerosis (Bourneville's Disease).

The "pharmaceutically acceptable carrier" means any pharmaceutically acceptable means to mix and/or deliver the targeted delivery composition to a subject. This includes a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and is compatible with administration to a subject, for example a human.

Administration to the subject can be either systemic or localized. This includes, without limitation, dispensing, delivering or applying an active compound (e.g. in a pharmaceutical formulation) to the subject by any suitable route for delivery of the active compound to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

It should be understood that this invention is not limited to the particular methodologies, protocols and reagents, described herein and as such may vary. The terminology used herein is for the purpose of describing particular embodiments only, and is not intended to limit the scope of the present invention, which is defined solely by the claims.

Therapeutic Administration and Formulations

It will be appreciated that administration of the purified populations of microvesicles associated with viral particles (MAV) in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The purified populations of microvesicles associated with viral particles (MAV) are administered to a subject, for example, a subject in need of gene therapy. Subjects are identified using any of a variety of clinical and/or laboratory tests such as, physical examination, radiologic examination and blood, urine and stool analysis to evaluate immune status.

Administration of the purified populations of microvesicles associated with viral particles (MAV) to a patient is considered successful if any of a variety of laboratory or clinical results is achieved. For example, administration of the purified populations of microvesicles associated with viral particles (MAV) to a patient is considered successful one or more of the symptoms associated with the disorder afflicting the patient is alleviated, reduced, inhibited or does not progress to a further, i.e., worse, state. Administration of the purified populations of microvesicles associated with viral particles (MAV) to a patient suffering from a disorder such is considered successful if the disorder enters remission or does not progress to a further, i.e., worse, state.

In some embodiments, the purified populations of microvesicles associated with viral particles (MAV) are administered in combination with a second agent, including for example, any of a variety of known anti-inflammatory and/or immunosuppressive compounds. In some embodiments, the purified populations of microvesicles associated with viral particles (MAV) are used in conjunction with a surgical method of treating or otherwise alleviating the disorder.

The purified populations of microvesicles associated with viral particles (MAV) are administered to a subject in an amount sufficient to have a desired modulation effect in the subject. In some embodiments, administration of the purified populations of microvesicles associated with viral particles (MAV) will abrogate or inhibit or otherwise interfere with at least one biological property and/or biological activity of a target.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1: Materials & Methods

Cell Culture:

293T human cells, U87 human glioma cells (both from American Type Culture Collection, Manassas, Va.) and Gli36 human glioma cells (kindly provided by Dr. Anthony Capanogni, University of California at Los Angeles, Los Angeles, Calif.), were maintained in Dulbecco's modified Eagle's medium (DMEM) supplemented with 10% fetal bovine serum (Sigma, St. Louis, Mo.), 100 U/ml penicillin, and 0.1 mg/ml streptomycin (Sigma), referred to as complete DMEM. All cells were grown at 37° C. in a 5% $CO_2$ humidified atmosphere.

Vector production and microvesicle isolation: AAV vectors were produced by transfecting 15 cm plates of 293T cells using the calcium phosphate method with the following plasmids: 12 μg of an ITR-flanked AAV transgene expression vector (green fluorescent protein, GFP or firefly luciferase, Fluc), 25 µg of an adenovirus helper plasmid Fd6 (Molecular Therapy (2005) 11, 843-848), and 12 µg of the AAV2 rep/cap expression vector, pH22 (Virology. February 2003, p. 2768-2774, Vol. 77, No. 4), or the AAV2rep/AAV1cap expression vector, pXR1 (from the UNC Gene Therapy Center). Sixteen hours post-transfection media was exchanged with fresh media supplemented with 2% microvesicle-depleted fetal bovine sera, FBS. Forty-eight to seventy-two hours post transfection media was harvested and microvesicles were purified as described below in "gradient centrifugation." Standard AAV was generated as previously described (Maguire C A et al., J Neurooncol. 2010 February; 96(3):337-47). The vector titer (in genome copies/ml [gc/ml]) was performed using a quantitative TaqMan PCR assay. First, AAV genomic DNA was isolated by treating a 2 µl microvesicle fraction in a 50 µl reaction with 2 units of DNaseI for 2 h at 37° C. to remove any potential extravesicular, unencapsidated AAV genomes or plasmid DNA. Next, DNase was inactivated for 25 min at 75° C. Then a PCR reaction was prepared using TaqMan® Fast Universal PCR Master Mix (Applied Biosystems, Foster City, Calif.), a TaqMan probe (5'-6FAM-TGCCAGC-CATCTGTTGTTTGCC-MGB Applied Biosystems) and primer set (forward primer, 5'-CCTCGACTGTGCCT-TCTAG-3'; reverse primer, 5'-TGCGATGCAATTTCCT-CAT-3') which specifically anneals to the Poly A signal sequence region in the transgene cassette. A standard curve was prepared using serial dilutions of an AAV plasmid of a known molar concentration. The quantitative PCR was performed in an Applied Biosystems 7500 Thermalcycler using the following conditions: 1 cycle, 94° C. 30 s; 40 cycles 94° C. 3 s, 60° C. 30 s.

Gradient centrifugation: Microvesicles were purified using a 6-18% iodixanol gradient as previously described (Cantin et al.) with the following modifications. The media harvested from AAV producer cells (293T) was centrifuged for 10 min. at 600×g. Media was then transferred to a fresh tube and centrifuged at 20,000×g for 25 min. The resulting microvesicle pellet was resuspended in 1 ml of phosphate buffered saline and treated with 250 U of Benzonase nuclease (Sigma) for 1 h at 37° C. A 6-18% iodixanol step gradient was prepared in 38.5 ml open-top thin-walled polyallomer tubes (Beckman, Palo Alto, Calif.) using Optiprep (Sigma-Aldrich, St. Lois, Mo.). After overlaying the gradient with one ml of the resuspended microvesicle pellet, the tubes were centrifuged at 32,000 rpm in a SW32 Ti rotor (Beckman-Coulter) for 129 min with the brake off in an Optima L-90K ultracentrifuge (Beckman-Coulter). Following the spin, the top 2 ml of the gradient were discarded and then 1 ml fractions from the top to the bottom of the gradient were collected.

Immunoblotting: After titration, a volume containing $10^8$ gc of AAV of the iodixanol gradient fraction was mixed with and added to SDS loading buffer. Samples were heated at 95° C. for 5 minutes. SDS-PAGE was performed using NuPAGE Novex 10% Bis-Tris acrylamide gels and MES running buffer. The gel was electrophoresed at 130V for 90 min. Following transfer of proteins to a nitrocellulose membrane, the membrane was blocked for 1 h in 10% milk in TBS/0.1% Tween-20. For AAV capsid protein immunoblotting membranes were probed with a 1:100 dilution of anti-adeno-associated virus VP1, VP2, VP3 antibody (American Research Products, Belmont, Mass.). A 1:5,000 dilution of anti-rabbit HRP conjugated secondary antibody (GE Healthcare) was used. Specific binding was detected using Pierce SuperSignal West Pico chemiluminescent substrate (Thermoscientific, Rockford, Ill.) and exposure of HyBlot CL autoradiography film (Denville Scientific, South Plainfield N.J.) to the membrane.

Vector transduction assays: $10^4$ cells (cell type indicated in figure) were plated the day before transduction in 96 well plates. Cell lysate (standard) purified AAV2 encoding firefly luciferase (Fluc), termed AAV2-Fluc, or microvesicle-associated AAV2-Fluc were mixed with media ($10^4$ gc/cell) in a total volume of 500 µl and added to cells. One hour later, media was removed and replaced with fresh media. After 48-72 h incubation at 37° C., cells were rinsed in PBS, lysed using Reporter Lysis Buffer (Promega, Madison, Wis.). A luciferase assay was performed on 20 µl of lysate using a luminometer equipped with an injector that added 100 ul of luciferase substrate buffer/well. Luciferase activities were normalized to protein content of the samples by performing a Bradford assay (BioRad, Hercules, Calif.).

GAPDH reverse transcriptase PCR: To detect mRNA inside microvesicles, $10^8$ g.c. of purified AAV2-Fluc associated microvesicles, were used to isolate RNA using Trizol LS reagent (Invitrogen). For a positive control, RNA was isolated from HeLa cells. Next a two-step reverse transcriptase PCR was performed using Sensiscript reverse transcriptase (Qiagen) and HotStarTaq DNA polymerase (Qiagen) was performed to amplify GAPDH transcripts from microvesicles RNA or from HeLa RNA. cDNA synthesis: 50 ng of RNA was used for template performed with Sensiscript reverse transcriptase (Qiagen). PCR amplification of GAPDH cDNA: 1 cycle 95° C. for 3 min; 40 cycles, 95° C. for 30 sec, 60° C. for 30 s, 70° C. for 30 s; 1 cycle 70° C. for 7 min. PCR products were analyzed on a 2% ethidium bromide-stained agarose gel.

RNA analysis for small RNA species: Extracted RNA was examined for small RNA species using a small RNA Bioanalyzer chip.

Nanoparticle tracking analysis (NTA): The size and concentration of nanoparticles in the microvesicle preparations was determined using a LM10-HS nanoparticle analyzer (Nanosight, Amesbury, UK) operated by NTA software. Samples were diluted in phosphate buffered saline and the particle size, particle concentration, and particle size distribution measured.

Example 2. Isolation, Purification and Characterization of Microvesicles Containing Viral Vectors 293T cells were transfected with AAV and helper plasmids to generate AAV vectors encoding green fluorescent protein (GFP). Forty-eight hours later, cells were prepared for transmission electron microscopy. Using plastic, embedded sectioned samples, microvesicles were observed on the outside of AAV-producer cells. Microvesicles were detected near the 293T producer cell surface. AAV particles were observed inside the microvesicles. Capsid-like structures were measured using software and determined to be 20-25 nm, which is the expected size of the AAV2 capsid.

In the methods used herein, the media was harvested from 293T cells producing AAV vectors and centrifuged at 300×g for 10 minutes to remove cells and other debris. The microvesicles and associated AAV were pelleted by centrifuging 20,000×g for 25 minutes, and the pellet was then resuspended in phosphate buffered saline and treated for 1 h at 37° C. with Benzonase to remove unprotected AAV DNA from transfection. The sample was then loaded onto a 6-18% iodixanol step gradient (in 1.2% step increments) and centrifuged in a SW32Ti swinging bucket rotor (Beckman Coulter) for 2 h 9 min at 32,000 rpm (no brake). The gradient was fractionated from top.

Standard purified AAV, i.e., cell lysates AAV, does not pellet efficiently using the centrifugation speed that is used for microvesicle pelleting (FIG. 1). Iodixanol-purified AAV isolated from cell lysates, which was presumably not associated with microvesicles, was centrifuged in DMEM 10% FBS containing media for 20,000×g for 25 minutes. Pelleting efficiency was determined by qPCR titration of AAV genomes in the media pre and post-centrifugation.

The AAV-microvesicle pellet was found to exhibit a different sedimentation velocity in iodixanol gradient as compared to cell lysate purified vector. Media from AAV producer cells (AAV vector encodes firefly luciferase (AAV-fluc)) was centrifuged for 25 min at 20,000×g and the media and microvesicle pellet were divided into separate samples and each loaded onto a separate 6-18% iodixanol step gradient. For comparison, cell lysate purified AAV-fluc was mixed with purified non-transfected 293T microvesicles and centrifuge on the gradient as described above. After centrifugation, each sample's gradient was divided into 1 ml fractions. An aliquot of each fraction was then added to separate wells containing 293T cells, and 48 hrs later cells were lysed and a luciferase assay performed to determine the fractions containing peak transgene (fluc) expression, Fraction 36.

Microvesicles from Fraction 36 were analyzed for size distribution by nanoparticle tracking analysis using a Nanosight particle analyzer. A large vesicle fraction was observed in the AAV associated-microvesicle samples but not the cell lysate purified AAV+microvesicle mix. The concentration of microvesicles was much higher in media from AAV producer cells as compared to nontransfected 293T.

The AAV associated-microvesicle pellet was shown to contain small RNA species in contrast to the cell lysates purified AAV and cell lysate purified AAV+microvesicle mix. Microvesicles from fraction 36 (see slide 6) were analyzed for the presence of small RNA species characteristic of microvesicles using a Bioanalyzer.

The AAV associated-microvesicles were shown to contain mRNA. Microvesicle Fraction 36 was analyzed for Glyceraldehyde 3-phosphate dehydrogenase (GAPDH) mRNA using reverse transcriptase PCR. RNA was extracted from a sample volume containing 1e8 genome copies of AAV as determined by quantitative real time PCR. A specific band of around 200 by was seen in samples containing microvesicles.

It was observed that the AAV associated-microvesicles contained AAV capsid proteins. A volume containing 1e8 genome copies of AAV from the microvesicle sample from Fraction 36 was loaded onto an SDS-PAGE gel. An immunoblot was performed using an anti-AAV capsid antibody to detect the three virus proteins, VP1, VP2, and VP3.

The AAV associated-microvesicles were shown to contain AAV genomes using analysis by quantitative PCR to detect the presence of AAV genomes.

Figure 2:
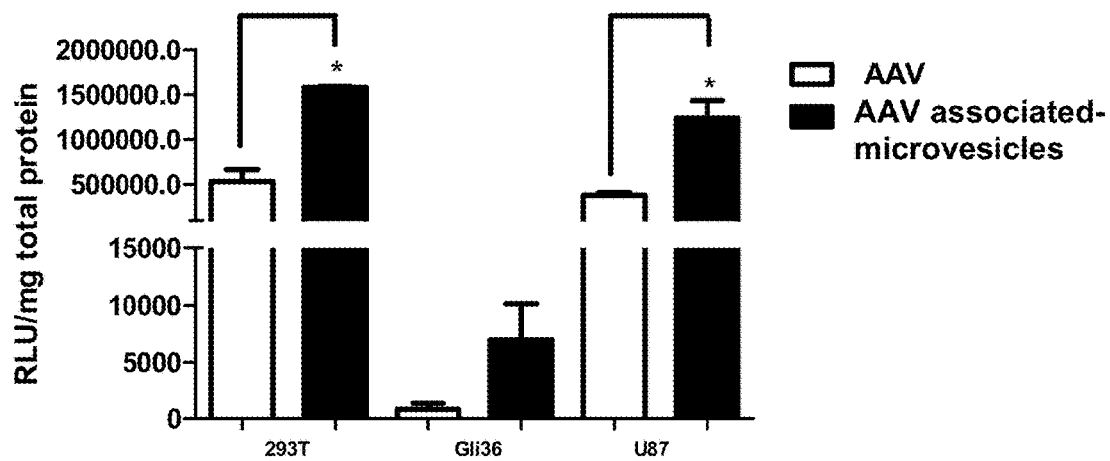
FIG. 2 is a graph depicting the ability of AAV associated-microvesicles to efficiently transduce cells in culture.

The AAV associated-microvesicles efficiently transduced cells in culture (FIG. 2). Cell-lysate purified AAV or AAV associated-microvesicles from Fraction 36 were used at equal doses ($10^4$ gc/cell) to transduce various cells in culture. The vectors encoded firefly luciferase (fluc) as a means of enabling measurement of transgene delivery and expression 48 hours post treatment.

To increase the yield of AAV associated-microvesicles, a DNA plasmid encoding vesicular stomatitis virus glycoprotein G (VSV-G) was co-transfected during AAV production in 293T cells. In three independent AAV associated-microvesicle preparations, the quantitative PCR genome copy titers in the presence and absence of the VSV-G plasmid during transfection were compared. A 5-65 fold enhancement in titer was observed when using the VSV-G plasmid.

Example 3: In Vivo Gene Expression in Purified AAV Associated-Microvesicles

In the studies described herein, the media from AAV producer cells was harvested 72 h post-transfection and spun at 300×g 10 min to remove cells and other debris. The AAV associated-microvesicles were pelleted by spinning at 20,000×g for 25 min. The pellet was then resuspended in 1×PBS (500 µl), and 50 µl 10×TURBO DNase Buffer and 10 µl Turbo DNase were added. The mixture was incubated for 30 min at 37° C. Then, 110 µl of resuspended DNase Inactivation reagent was added and mixed thoroughly. The mixture was then mixed occasionally at room temperature for 5 min. The mixture was then centrifuged at 2,000×g for 1.5 min, and the supernatant was transferred to a fresh tube. The supernatant was kept on ice, titered and injected into mice.

Figure 3A:
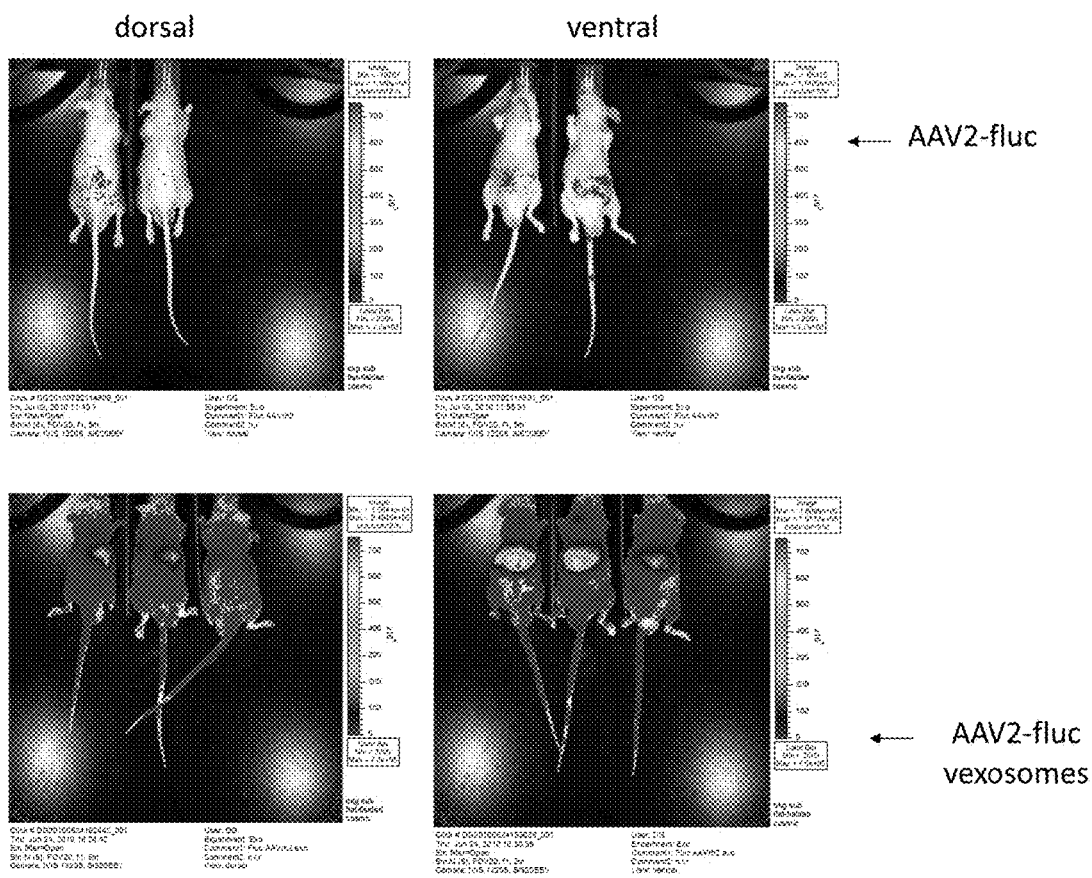
FIGS. 3A and 3B are an illustration and a graph depicting the ability of AAV associated-microvesicles to efficiently transduce cells in vivo.
Figure 3B:
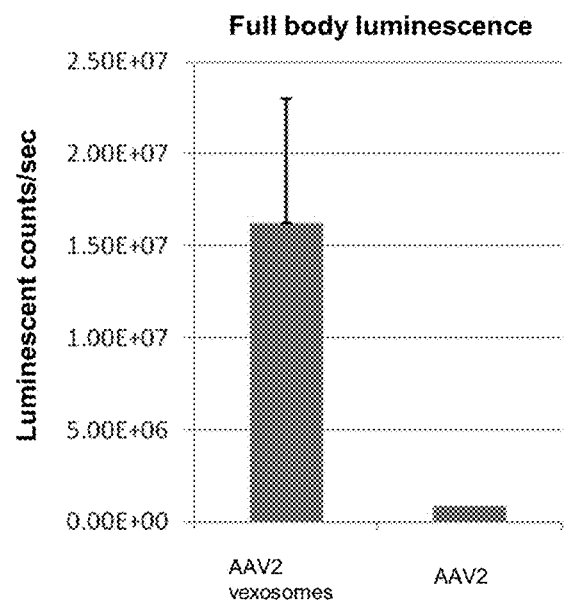
Figure 4A:
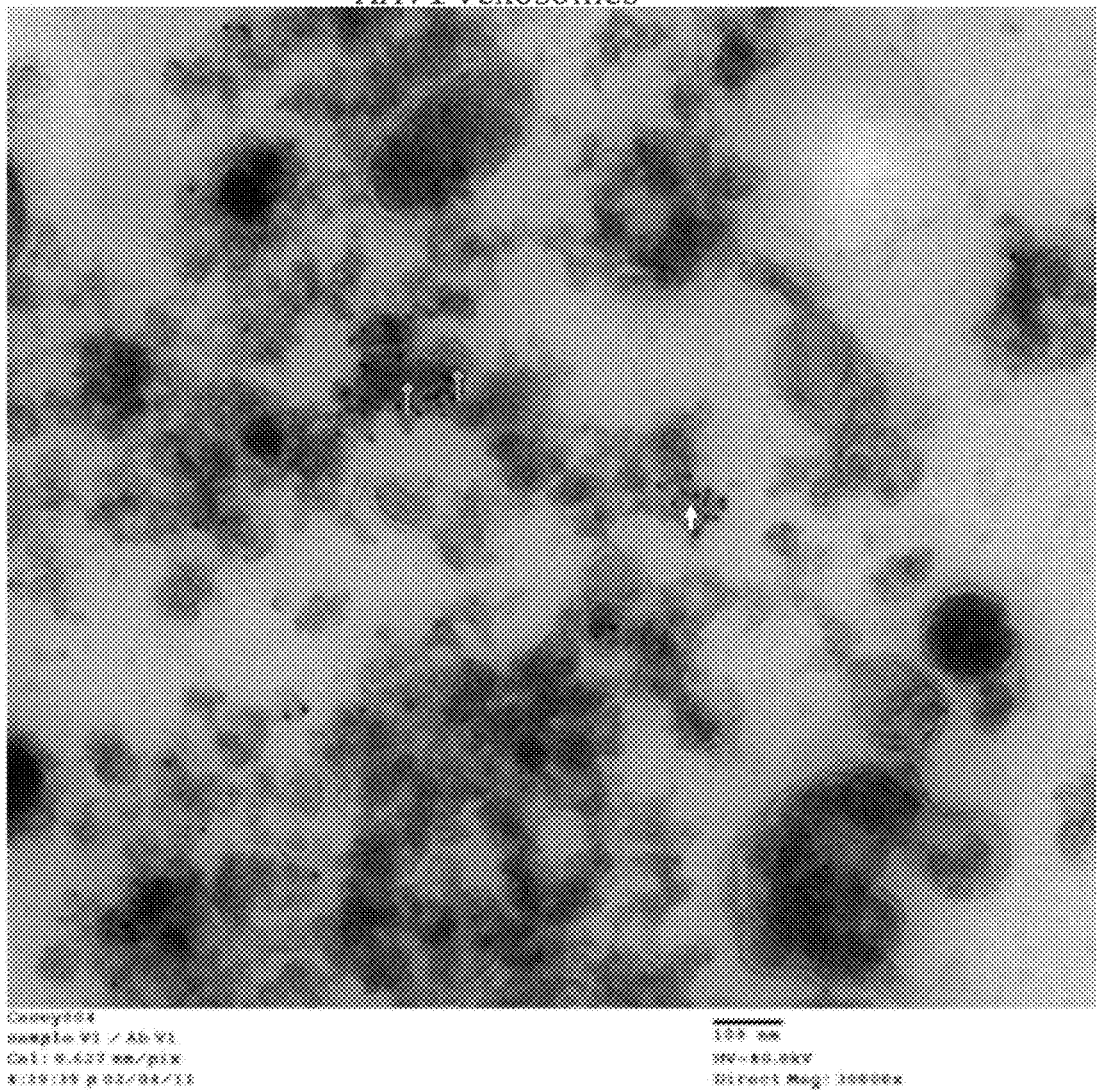
FIGS. 4A-4E are a series of illustrations depicting the use of anti-AAV immunogold labeling in the detection of microvesicle-associated vectors. In these illustrations, the arrows are indicating the location of AAV (AAV1 or AAV2) that is "free," i.e., outside of a microvesicle, the triangles are indicating the location of AAV (AAV1 or AAV2) inside a microvesicle, and the diamond-headed arrows are indicating the location of AAV (AAV1 or AAV2) that is bound to surface of a microvesicle.
Figure 4B:
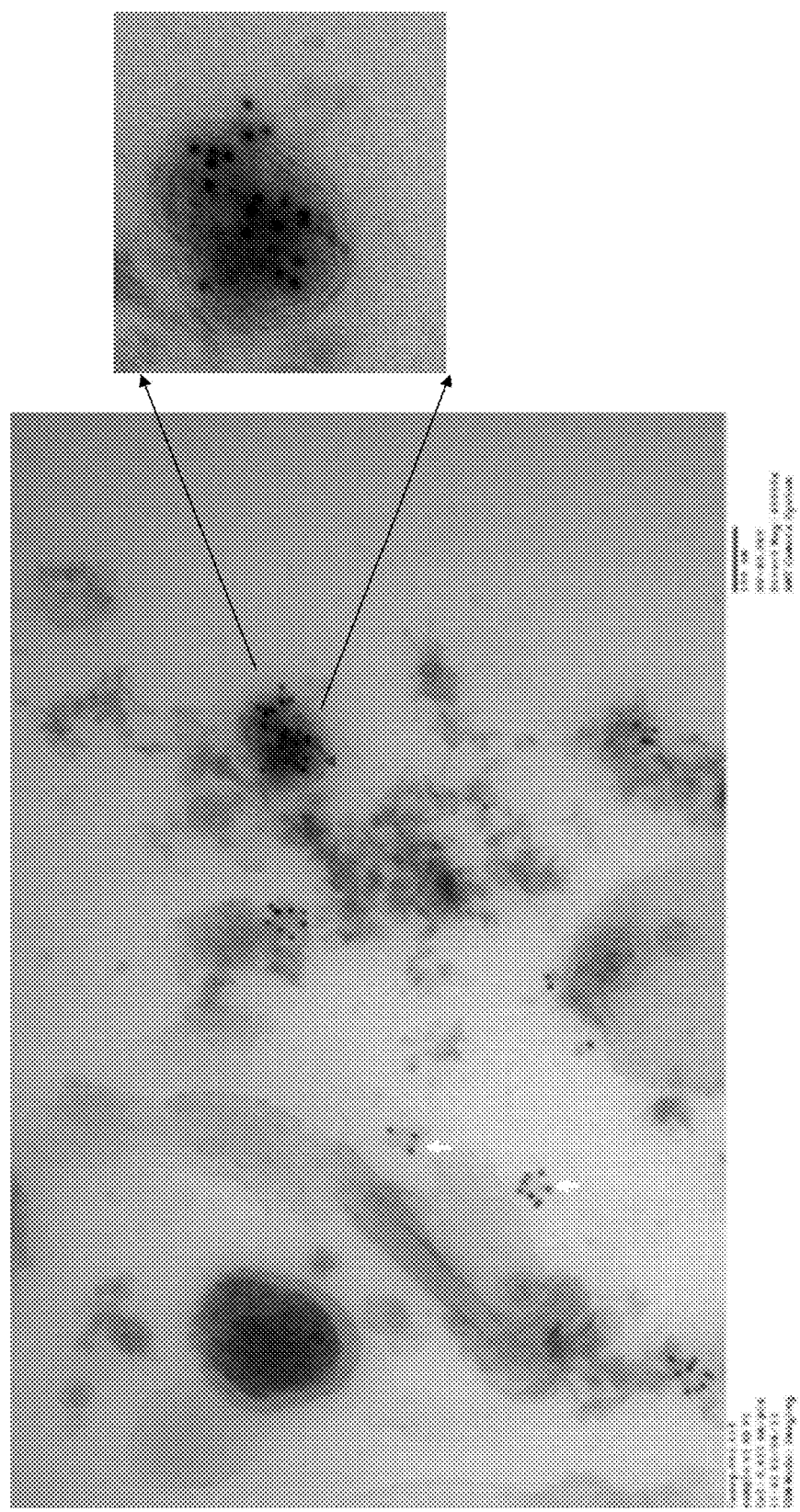
Figure 4C:
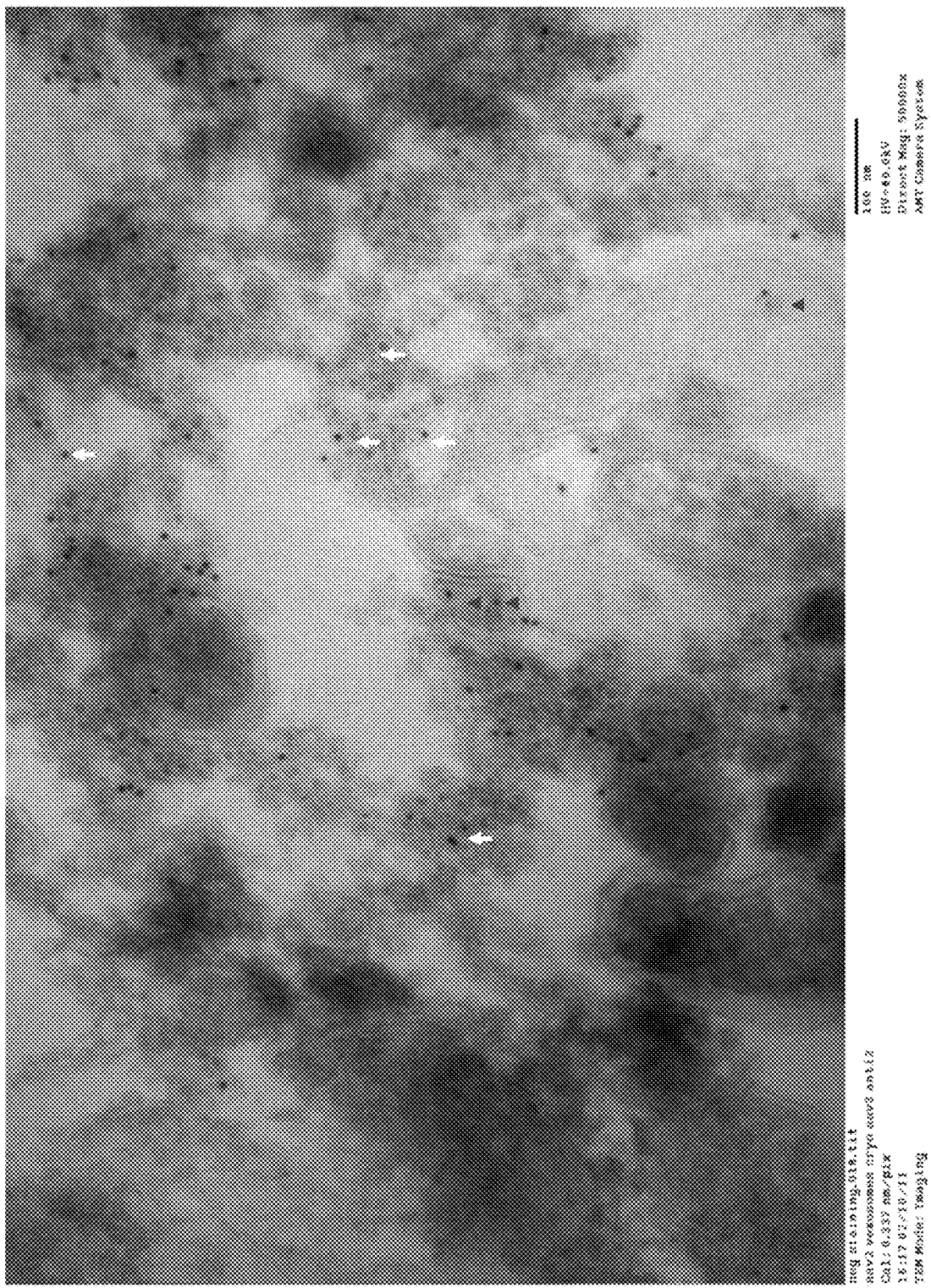
Figure 4D:
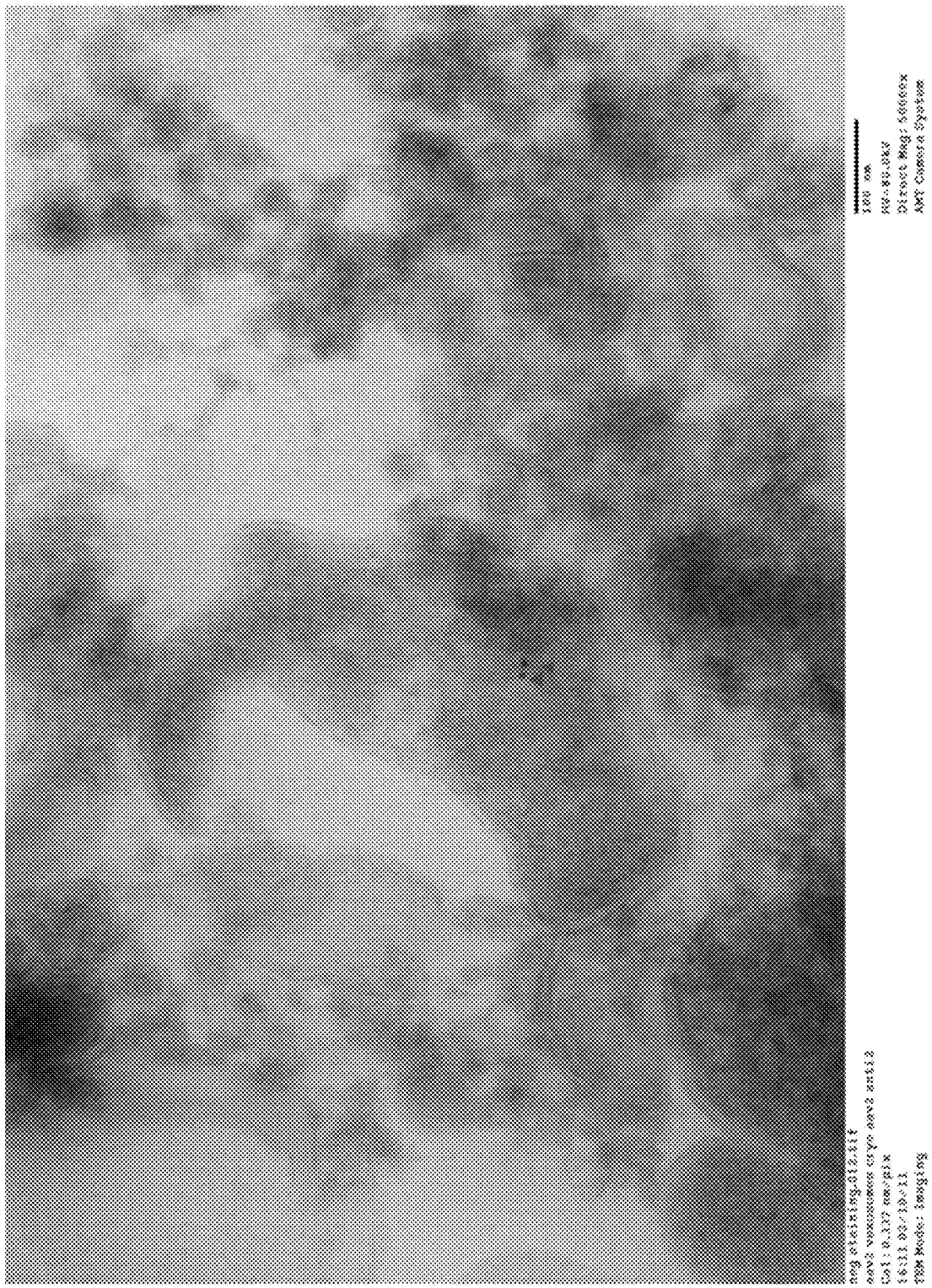
Figure 4E:
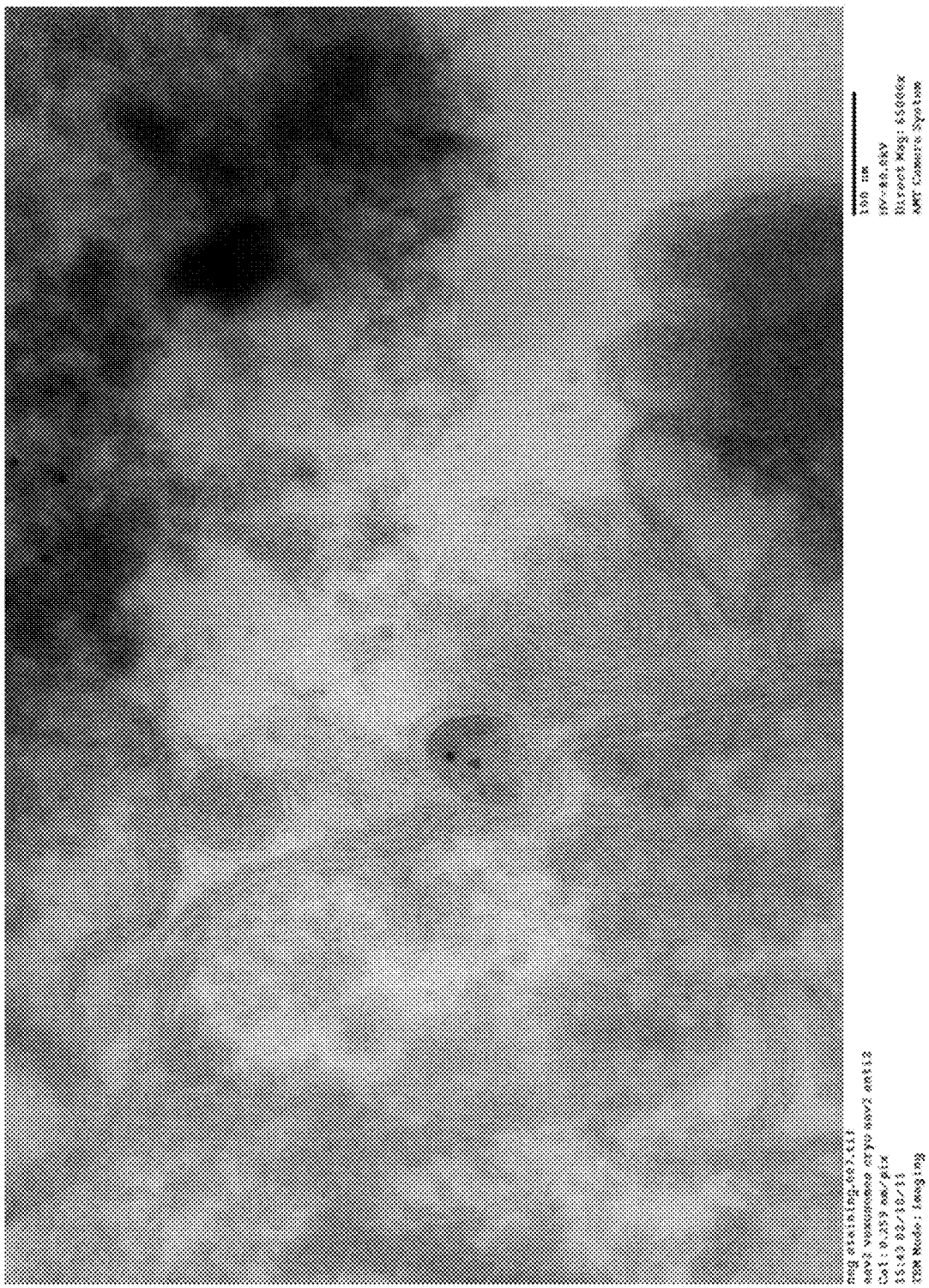

$2 \times 10^9$ genome copies of standard cell lysate purified AAV2-fluc or AAV2-fluc AAV associated-microvesicles were injected via the tail vein of nude mice. Two weeks post injection, d-luciferin was injected intraperitoneally, and fluc expression was detected with bioluminescence imager (FIGS. 3A, 3B).

Example 4: Immunogold Labeling and Detection of AAV Associated Microvesicles

Cryosections of microvesicle associated vectors that contained either an AAV1 vector or an AAV2 vector (i.e., both AAV1 and AAV2 serotypes were tested) were stained with commercially available anti-AAV1 and anti-AAV2 antibodies followed by a secondary antibody labeled with 10 nm gold. In this study, the anti-AAV2 antibody served as a negative control for AAV1, while the anti-AAV1 antibody served as a negative control for AAV2. No immunogold labeling was observed for negative controls. The sections were then imaged by transmission electron microscopy.

The results of this study are shown in FIGS. 4A-4E. In these figures, the arrows are indicating the location of AAV (AAV1 or AAV2) that is "free," i.e., outside of a microvesicle, the triangles are indicating the location of AAV (AAV1 or AAV2) inside a microvesicle, and the diamond-headed arrows are indicating the location of AAV (AAV1 or AAV2) that is bound to surface of a microvesicle. As shown in FIGS. 4A-4E, AAV capsids were detected inside microvesicles for both AAV1 and AAV2 serotypes, and a lot of free AAV capsids were also detected.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified population of microvesicles associated with one or more viral vector particles, wherein the microvesicle associated with the one or more viral vector particles is shed by a producer cell engineered to comprise the one or more viral vector particles, wherein the one or more viral vector particles are or are derived from adeno-associated virus (AAV), and wherein the one or more viral vector particles comprises a nucleic acid that is exogenous to the one or more viral vector particles.

2. The purified population of claim 1, wherein the producer cell naturally sheds the microvesicles associated with the one or more viral vector particles.

3. The purified population of claim 1, wherein the producer cell has been modified to shed the microvesicles associated with the one or more viral vector particles.

4. The purified population of claim 1, wherein the microvesicle comprises a lipid membrane having an outer surface that has been modified to include or express a receptor ligand or bridging molecule linked to a receptor ligand that targets a desired cell type.

5. The purified population of claim 4, wherein the desired target cell type is different from that of the cell type that is targeted by a microvesicle having an unmodified lipid membrane.

6. The purified population of claim 1, wherein the population of microvesicles comprises about $10^9$ to $10^{13}$ viral vector genome copies.

7. The purified population of claim 1, wherein the nucleic acid that is exogenous to the viral vector particle is RNA or DNA.

8. The purified population of claim 7, wherein the RNA is RNAi, shRNA, siRNA, miRNA, or a combination thereof.

9. The purified population of claim 1, wherein the nucleic acid that is exogenous to the one or more viral vector particles encodes a peptide, polypeptide or protein.

10. The purified population of claim 1, wherein the producer cell is engineered to comprise the one or more viral vector particles by transient transfection.

11. The purified population of claim 1, wherein the producer cell is engineered to comprise the one or more viral vector particles by stable transfection.

12. A purified population of microvesicles associated with one or more adeno-associated virus (AAV) vector particles, wherein the microvesicles associated with the one or more AAV vector particles are shed by a producer cell engineered by transient transfection to comprise the one or more AAV vector particles, wherein the one or more AAV vector particles comprise a nucleic acid that is exogenous to the one or more AAV vector particles.

13. The purified population of claim 12, wherein the producer cell naturally sheds the microvesicles associated with the one or more AAV vector particles.

14. The purified population of claim 12, wherein the producer cell has been modified to shed the microvesicles associated with the one or more AAV vector particles.

15. The purified population of claim 12, wherein the microvesicle comprises a lipid membrane having an outer surface that has been modified to include or express a receptor ligand or bridging molecule linked to a receptor ligand that targets a desired cell type.

16. The purified population of claim 12, wherein the population of microvesicles comprises about $10^9$ to $10^{13}$ AAV vector genome copies.

17. The purified population of claim 1, wherein the microvesicles are from 10 nm to 5000 nm in diameter.

18. The purified population of claim 1, wherein the microvesicles are from 10 nm to 1000 nm in diameter.

19. The purified population of claim 1, wherein the microvesicles are from 30 nm to 200 nm in diameter.

20. The purified population of claim 1, wherein the microvesicles are from 30 nm to 800 nm in diameter.

21. The purified population of claim 12, wherein the microvesicles are from 10 nm to 5000 nm in diameter.

22. The purified population of claim 12, wherein the microvesicles are from 10 nm to 1000 nm in diameter.

23. The purified population of claim 12, wherein the microvesicles are from 30 nm to 200 nm in diameter.

24. The purified population of claim 12, wherein the microvesicles are from 30 nm to 800 nm in diameter.

* * * * *